US007867497B2

(12) United States Patent
Crowe, Jr.

(10) Patent No.: US 7,867,497 B2
(45) Date of Patent: Jan. 11, 2011

(54) MONOCLONAL ANTIBODIES TO RESPIRATORY SYNCYTIAL VIRUS AND USES THEREFOR

(75) Inventor: James E. Crowe, Jr., Nashville, TN (US)

(73) Assignee: Vanderbilt University, Nashville, TN (US)

( * ) Notice: Subject to any disclaimer, the term of this patent is extended or adjusted under 35 U.S.C. 154(b) by 96 days.

(21) Appl. No.: 12/236,245

(22) Filed: Sep. 23, 2008

(65) Prior Publication Data

US 2009/0092609 A1  Apr. 9, 2009

Related U.S. Application Data

(60) Provisional application No. 60/974,673, filed on Sep. 24, 2007.

(51) Int. Cl.
   *A61K 39/42*  (2006.01)
   *C12Q 1/70*  (2006.01)
   *C07K 16/10*  (2006.01)
   *C07K 16/46*  (2006.01)
   *C12N 15/13*  (2006.01)

(52) U.S. Cl. .................. 424/147.1; 424/135.1; 435/5; 530/387.3; 530/388.3; 536/23.53

(58) Field of Classification Search ....................... None
   See application file for complete search history.

(56) References Cited

U.S. PATENT DOCUMENTS

| 5,639,641 | A | 6/1997 | Pedersen et al. | 435/69.6 |
|---|---|---|---|---|
| 5,824,307 | A | 10/1998 | Johnson | 424/133.1 |
| 5,861,155 | A | 1/1999 | Lin | 424/133.1 |
| 5,922,344 | A | 7/1999 | Hilty et al. | 424/439 |
| 6,180,377 | B1 | 1/2001 | Morgan et al. | 424/133.1 |
| 6,491,916 | B1 | 12/2002 | Bluestone et al. | 424/133.1 |
| 6,632,927 | B2 | 10/2003 | Adair et al. | 530/387.3 |
| 6,656,467 | B2 | 12/2003 | Young et al. | 424/147.1 |
| 6,685,942 | B1 | 2/2004 | Burton et al. | 424/159.1 |
| 6,818,216 | B2 | 11/2004 | Young et al. | 424/159.1 |
| 6,855,493 | B2 | 2/2005 | Young et al. | 435/5 |
| 7,488,477 | B2 | 2/2009 | Pilkington et al. | 424/147.1 |
| 2004/0005323 | A1 | 1/2004 | Brams | 424/159.1 |
| 2004/0005324 | A1 | 1/2004 | Pilkington et al. | 424/159.1 |

FOREIGN PATENT DOCUMENTS

| EP | 1 659 133 | 5/2006 |
|---|---|---|
| EP | 1 997 830 | 12/2008 |
| WO | WO 2004/076677 | 9/2004 |
| WO | WO 2006/034292 | 3/2006 |
| WO | WO 2006/050280 | 5/2006 |
| WO | WO 2007/101441 | 9/2007 |

OTHER PUBLICATIONS

Groothuis et al., "Prophylactic administration of respiratory syncytial virus immune globulin to high-risk infants and young children. The Respiratory Syncytial Virus Immune Globulin Study Group," *New Engl. J. Med.*, 329:1524-1530, 1993.

Johnson et al., "Development of a humanized monoclonal antibody (MEDI-493) with potent in vitro and in vivo activity against respiratory syncytial virus," *J. Infect. Diseases*, 176:12151224, 1997.

Murphy et al., "An update on approaches to the development of respiratory syncytial virus (RSV) and parainfluenza virus type 3 (PIV3) vaccines," *Virus Res.*, 32:13-36, 1994.

Murphy et al., "Effect of passive antibody on the immune response of cotton rats to purified F and G glycoproteins of respiratory syncytial virus (RSV).," *Vaccine*, 9:185-189, 1991.

Murphy et al., "Passive transfer of respiratory syncytial virus (RSV) antiserum suppresses the immune response to the RSV fusion (F) and large (G) glycoproteins expressed by recombinant vaccinia viruses," *J. Virol.*, 62:3907-3910, 1988.

Prince et al., "Immunoprophylaxis and immunotherapy of respiratory syncytial virus infection in the cotton rat," *Virus Res.*, 3:193-206, 1985.

Prince et al., "Mechanism of antibody-mediated viral clearance in immunotherapy of respiratory syncytial virus infection of cotton rats," *J. Virol.*, 64:3091-3092, 1990.

Prince et al., "Mechanisms of immunity to respiratory syncytial virus in cotton rats," *Infect. Immun.*, 42:81-87, 1983.

Prince et al., "Quantitative aspects of passive immunity to respiratory syncytial virus infection in infant cotton rats," *J. Virol.*, 55:517-520, 1985.

The Prevent Study Group, "Reduction of respiratory syncytial virus hospitalization among premature infants and infants with bronchopulmonary dysplasia using respiratory syncytial virus immune globulin prophylaxis. The PREVENT Study Group," *Pediatrics*, 99:93-99, 1997.

International Search Report and Written Opinion issued in Application No. PCT/US2008/077370, dated Jan. 21, 2009.

International Preliminary Report on Patentability for PCT/US2008/077721, mailed Mar. 30, 2010.

*Primary Examiner*—Mary E Mosher
(74) *Attorney, Agent, or Firm*—Fulbright & Jaworski (57) ABSTRACT

The present invention is directed to particular human monoclonal antibodies and fragments thereof that find use in the detection, prevention and treatment of respiratory syncytial virus infections. In particular, these antibodies may neutralize RSV. Also disclosed are improved methods for producing monoclonal antibodies.

22 Claims, 2 Drawing Sheets

MONOCLONAL ANTIBODIES TO RESPIRATORY SYNCYTIAL VIRUS AND USES THEREFOR

This application claims benefit of priority to U.S. Provisional Application Ser. No. 60/974,673, filed Sep. 24, 2007, the entire contents of which are hereby incorporated by reference.

This invention was made with government support under grant number R01 AI-48677 awarded by the National Institutes of Allergy and Infectious Disease and the National Institutes of Health. The government has certain rights in the invention.

BACKGROUND OF THE INVENTION

1. Field of the Invention

The present invention relates generally to the fields of virology, immunology and pathology. More particularly, it concerns the development of human monoclonal antibodies for use in the diagnosis, prevention and therapy of respiratory syncytial virus infections.

2. Description of Related Art

Human respiratory syncytial (RSV) virus is a pneumovirus in the family Paramyxoviridae. It is a non-segmented negative-strand RNA virus, with a cytoplasmic replication program. The viral nucleocapsid is packaged in a lipid envelope that is acquired from the host cell plasma membrane during budding. The virus has a fusion protein (RSV F) and a highly glycosylated attachment G glycoprotein (RSV G). RSV can infect cells as a cell-free virus, but can also spread by syncytium formation between infected cells and uninfected neighboring cells. Membrane fusion is important for both virus entry and for cell-to-cell spread.

RSV is the leading viral cause of severe lower respiratory tract illness in infants and young children (Walsh and Graham, 1999). RSV can also cause severe illness and death in the elderly (Treanor and Falsey, 1999) and immunocompromised bone marrow (Hertz et al., 1989; Wendt et al., 1995) and lung transplant patients (Wendt et al., 1995). The mortality rate in bone marrow transplant patients has been reported to be between 70 and 100% (Hertz et al, 1989).

Although RSV-induced disease in infants may be primarily immune-mediated, in bone marrow and lung transplant recipients and in persons with severe combined immunodeficiency syndrome the pathology, characterized by giant cell formation, is related to ongoing viral replication. In addition, infants with AIDS have been shown to have continuous viral shedding for over 200 days (King et al., 1993). These patient groups would benefit from more effective antiviral therapeutic options for RSV, and it is even more likely that antiviral prophylaxis would have an impact on illness in infants and the elderly.

SUMMARY OF THE INVENTION

The invention comprises a unique human monoclonal antibody that binds the respiratory syncytial virus fusion protein, generated by an optimized procedure for producing human monoclonal antibodies. In one embodiment, the invention comprises a nucleic acid molecule encoding a heavy chain variable region comprising:

```
                                        (SEQ ID NO: 2)
EVQLVESGGGLAQPGGSLTLACAASGFTFSYNMHWVRQAPGKGLEWVSY

ITSNSLNIYYADSVKGRFTISRDNAKNSLYLRMHSLSDEDTSVYYCARDS

SGSIGWSDPLDYWGQGTLVTVSSAGT
```

Also provided is nucleic acid molecule encoding a light chain variable region comprising:

```
                                        (SEQ ID NO: 4)
DIVLTQTPGTLSVSPGERATLSCRASQSVSSNLAWYQQKPGQAPRLLISG

ASTRATGIPARFSGSGSGTEFTLTISSLQSEDFAVYYCQQYNYWPPWTFG

QGTKLEIKRTV
```

Further, an antibody, single chain antibody, Fab' antibody fragment or F(ab')₂ antibody fragment comprising both heavy and light chain variable regions as specified above are provided. The antibody or antibody fragment may be dispersed in a pharmaceutically acceptable carrier. In particular, the nucleic acid sequences may comprise:

```
RSV G8 heavy chain
                                        (SEQ ID NO: 1)
GAGGTGCAGCTGGTGGAGTCTGGGGGAGGCTTGGCACAGCCTGGGGGGTC

CCTGACACTCGCCTGTGCAGCCTCTGGATTCACCTTCACTAGTTATAACA

TGCACTGGGTCCGCCAGGCTCCGGGGAAGGGGCTGGAGTGGGTTTCATAC

ATTACTAGTAATAGTCTTAACATATACTACGCAGACTCTGTGAAGGGCCG

ATTCACCATCTCCAGAGACAATGCCAAGAATTCACTGTATCTGCGAATGC

ACAGCCTGAGCGACGAGGACACGTCTGTGTATTACTGTGCGCGAGACTCG

TCCGGCAGTATTGGCTGGTCCGACCCCCTTGATTACTGGGGCCAGGGAAC

CCTGGTCACCGTCTCCTCAGCCGGTACCAA

RSV G8 light chain
                                        (SEQ ID NO: 3)
GATATTGTGCTGACTCAGACTCCAGGCACCCTGTCTGTATCTCCAGGGGA

AAGAGCCACCCTCTCCTGCAGGGCCAGCCAGAGCGTTAGCAGCAATTTAG

CCTGGTACCAGCAGAAACCTGGGCAGGCTCCCAGGCTCCTCATCTCTGGT

GCATCCACCAGGGCCACTGGTATCCCAGCCAGGTTCAGTGGCAGTGGGTC

TGGGACAGAGTTCACTCTCACCATCAGCAGCCTACAGTCTGAAGATTTTG

CAGTCTATTACTGTCAGCAGTATAATTACTGGCCTCCGTGGACGTTCGGC

CAAGGGACCAAGCTGGAGATCAAACGTACTGTG
```

The antibody neutralizes RSV in a 60% plaque reduction neutralizing test at a concentration of 0.2 µg/ml.

In another embodiment, there is provided a method of neutralizing respiratory syncytial virus (RSV) comprising contacting said virus with an antibody or antibody fragment having heavy and light chain variable regions as set forth above. The antibody may be a single chain antibody, and the antibody fragment may be a Fab' or F(ab')₂. The contacting may occur in vitro or in vivo. The RSV may be is located in a human subject, such as an infant or child. The method may further comprising administering to said subject an antiviral. The antibody or antibody fragment may be is administered to said subject more than once. The antibody or antibody fragment may be administered intravenously. The antibody or antibody fragment may prevent or reduce the severity of infection in said subject by RSV.

In yet another embodiment, there is provided a method of diagnosing a respiratory syncytial virus (RSV) infection in a subject comprising (a) obtaining a sample from said subject; (b) contacting said sample with an antibody or antibody fragment with heavy and light chain variable regions as specified in claims 1 and 2, respectively; and (c) determining the presence of an RSV antigen bound to said antibody. Steps (b) and (c) may comprise an ELISA, RIA or FIA. The subject may be at risk of exposure to RSV or may previously have had RSV infection. The method may further comprise making a treatment and/or quarantine decision for said subject based on step (c).

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Invention

As discussed above, respiratory syncytial (RSV) virus is the leading viral cause of severe lower respiratory tract illness in infants and young children (Walsh and Graham, 1999), and can also cause severe illness and death in the elderly (Treanor and Falsey, 1999) and immunocompromised bone marrow (Hertz et al., 1989; Wendt et al., 1995) and lung transplant patients (Wendt et al., 1995). The mortality rate is extremely high in bone marrow transplant patients (Hertz et al., 1989). All of these patient groups would benefit from more effective antiviral therapeutic options for RSV.

The present invention provides a new human monoclonal antibody that can be delivered in the same manner as currently approved anti-viral therapies for RSV. The antibody binds to the virus fusion protein and causes neutralization of viral infectivity.

II. Respiratory Syncytial Virus

A. General

As discussed above, human respiratory syncytial (RSV) virus is a pneumovirus in the family Paramyxoviridae, having a non-segmented negative-strand RNA virus, with a cytoplasmic replication program. RSV can infect cells as a cell-free virus, but can also spread by syncytium formation between infected cells and uninfected neighboring cells. Thus, membrane fusion is important for both virus entry and for cell-to-cell spread. RSV is the leading viral cause of severe lower respiratory tract illness in infants and young children (Walsh and Graham, 1999). RSV can also cause severe illness and death in the elderly (Treanor and Falsey, 1999) and immunocompromised bone marrow (Hertz et al., 1989; Wendt et al., 1995) and lung transplant patients (Wendt et al., 1995). The mortality rate in bone marrow transplant patients has been reported to be as high as between 70% and 100% (Hertz et al, 1989).

Although RSV-induced disease in infants may be primarily immune-mediated, in bone marrow and lung transplant recipients and in persons with severe combined immunodeficiency syndrome the pathology, characterized by giant cell formation, is related to ongoing viral replication. In addition, infants with AIDS have been shown to have continuous viral shedding for over 200 days (King et al., 1993). These patient groups would benefit from more effective antiviral therapeutic options for RSV. It is more likely that antiviral prophylaxis would be required to make an impact on illness in infants and the elderly.

RSV G is thought to be the attachment glycoprotein of RSV, although the host cell receptor has never been identified definitively. A cold-passaged B-strain RSV has been shown to infect cells having a deleted G, indicating that other RSV proteins may be sufficient for RSV attachment. One of these other proteins, RSV F, is thought to be trimeric with oligomers composed of three transmembrane virion protein molecules assembled separately to make up the membrane spikes. RSV G and the small hydrophobic protein (RSV SH) may also be part of the membrane spike structure. The F protein contains a cleaved N terminal signal sequence. The protein requires endoproteolytic cleavage into F1 and F2 to be functional. Results of recent experiments, indicating that whole RhoA enhances viral infection of cells, but that RhoA peptide from the fusion protein binding region inhibits viral infection, suggest that RhoA may be a host cell RSV receptor or coreceptor. These results are described in copending U.S. Ser. No. 09/129,565.

B. Models

Rodent models of RSV have been used to study pathogenesis and to evaluate candidate vaccines and anti-viral agents including passive antibody approaches. The mouse and cotton rat have been especially accurate in predicting the clinical response to anti-viral agents active against RSV. Preclinical studies in the mouse model show that it accurately reflects the behavior of therapeutic products in subsequent clinical trials (Graham et al., 1993, 1995; Fisher et al., 1999). Moreover, the assessment of RSV treatments in African Green Monkeys or Chimpanzees is prohibitively expensive, and no more predictive than the rodent models for testing the anti-viral effects of agents active against RSV.

C. Treatments

RSV infections that are mild are usually self-limiting. This means that once an infection occurs, it must "run its course." RSV infections in infants and children are generally mild in nature and can be treated at home. For mild infections, treatment focuses on alleviating the symptoms such as fever, cough, and congestion. It is important to be sure that the infant is able to breath, drink, eat and sleep comfortably.

More severe RSV infections that compromise a child's breathing may require hospitalization. Children who have difficulty breathing and require hospitalization may also require supplemental oxygen therapy. Oxygen is frequently supplied through a mask or nasal prongs. Breathing treatments are commonly used to help open the airways. An instrument called a nebulizer may be used to help deliver medication deep into the lungs. Medications most frequently used for breathing treatments are $\beta 2$ agonists (such as albuterol). $\beta 2$ agonists work by helping open the airways in the lungs allowing for more oxygen to enter the lungs, thereby enabling the child to breath easier.

Corticosteroids are also frequently used to treat RSV. They are used to reduce the inflammation in the lungs that leads to difficulty breathing. However, most clinical studies failed to show consistent evidence of clinical improvement after their use. Older children and children with a history of airway disease are more likely to benefit from corticosteroids, and it is recommended that corticosteroids only be used in such individuals.

The only licensed product for treating severe RSV infection is ribavirin, which has been demonstrated in rodent models (Wyde et al., 1987; Gruber et al., 1987). Several antibody products have been licensed for prophylactic treatment of RSV in selected risk groups. In particular, MEDI-524, or Numax™, is being tested in multicenter clinical trials. Another MCG product, MEDI-494, marketed as Synagis®, has become a standard treatment that has cut hospitalization of these at-risk infants in half.

III. Producing Monoclonal Antibodies

A. General Methods

It will be understood that monoclonal antibodies binding to RSV and related proteins will have utilities in several applications. These include the production of diagnostic kits for use in detecting and diagnosing disease. In these contexts, one may to link such antibodies to diagnostic or therapeutic agents, or use them as capture agents or competitors in competitive assays. Means for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host. As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of nonspecific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

In the case of human monoclonal antibodies, one may instead simply look for an individual already known to have generated an immune response, in this case, to have been infected with RSV. Virtually all adults have significant serum titers of neutralizing antibodies to RSV, therefore most adults are candidates to donate blood containing B cells from which our method can generate human monoclonal antibodies. The antibody described in this invention was generated in this way, by using peripheral blood from an otherwise healthy individual previously infected with RSV.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658; K6H6/B5 (ATCC CRL-1823 SHM-D33

(ATCC CRL-1668) and HMMA2.5 (Posner et al., 1987). HMMA2.5, the line used to generate the antibody in this invention, was generated by fusion of the mouse myeloma cell line P3x63Ag8.653 with bone marrow mononuclear cells from a patient with IgA myeloma. HMMA2.5 was modified from HMMA2.11TG/O. The final line generated, HMMA2.5, was used by the inventor to generate the RSV antibody hybridoma described here. For additional information, see Posner et al., *Hybridoma* 6, 611-625 (1987).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986).

Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as FPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Improved Methods of Antibody Production

The antibody of the present invention was prepared with an optimized electrofusion method using a PA-4000/PA-101 apparatus with electrode FE-20/1000 fusion chambers (Cyto Pulse Sciences, Inc.). Fusion volume was 500 µl. The myeloma cells and EBV-transformed human B cells were washed with RPMI-1640 and Cytofusion medium (Cyto Pulse Sciences, Inc.). Instrument settings were as follows. Pre-fusion dielectrophoresis was performed for 15 seconds with an alternating current voltage of 70V at 0.8 Mhz. Cells were electroporated with a single square-wave high-voltage direct current pulse lasting 0.04 milliseconds. The pulse frequencies and voltages we testede included a single pulse of 300V or multiple pulses of different decreasing voltages from 280V to 260V. Post-fusion dielectrophoresis was accomplished for 30 seconds using an alternating current voltage of 20V at 0.08 Mhz. After fusion, cells were allowed to recover in the fusion electrode for 30 minutes at room temperature, harvested, and then washed once with RPMI-1640 prior to plating in multi-well plates for culture.

After fusion, cells were seeded into 96-well microplates at approximately 6,000 B cells per well (for example 18,000 total cells when a 2:1 myeloma to B cell ratio was used in fusion) in complete RPMI-1640 medium containing 20% heat-inactivated FBS, 2.5 µg/ml amphotericin B, 2 mM L-glutamine, 1 mM sodium pyruvate, 50 µg/ml gentamicin, 60 µg/ml tylosin solution, 100 µM hypoxanthine, 0.4 µM aminopterin, 16 µM thymidine (HAT; Sigma) and 0.5 µM ouabain. After seven days of culture, cells were fed by removing 100 μl culture medium followed by addition of an equal volume of fresh medium containing 100 μM hypoxanthine/16 μM thymidine (HT; Sigma). The number of independent colonies in each well was counted 20 days after fusion. Fusion efficiency on a percentage basis was calculated as the mean number of hybridoma colonies per number of input B cells×100. After initial screening for immunoglobulin (Ig) production by an enzyme-linked immunosorbent assay (ELISA), the hybridoma cells from positive wells were expanded into 24-well plates and cultured in RPMI 1640 containing 20% heat-inactivated FBS, 2 mM glutamine, 1 mM sodium pyruvate and 50 μg/mL gentamicin. Supernatants of the expanded lines then were tested for specificity using an antigen-specific ELISA. The positive hybridoma cells were sub-cloned by serial limiting dilution in 96-well plates at 100, 10, and 0.3 cell-per-well density. The 0.3 cell-per-well limiting dilutions were performed twice to ensure that we generated clones.

To establish optimal drug treatment conditions for selection of human hybridomas, the inventors determined the sensitivity and resistance to drug selection of both transformed B cells and myeloma fusion partner cell lines. Conventional primary B cells die in prolonged culture, but transformed B cells can survive prolonged culture and HAT selection. Human cells are sensitive to ouabain selection, however, therefore the selection of human hybridomas was carried out in the presence of ouabain to eliminate non-fused EBV-transformed B cells. The inventors tested the sensitivity of EBV-transformed human B cells to differing concentrations of ouabain and found the minimum concentration for killing EBV-transformed human B cells to be 0.5 μM. More than 99% of EBV-transformed B cells were killed during seven days of culture in medium containing 0.5 μM ouabain. The inventors then tested the resistance of seven myeloma fusion partner cell lines to 0.5 μM ouabain. The results showed the Sp2/0 mL-6 (hTERT), SDM-D33, HMMA 2.5 and KR12 cell lines grew normally after seven days of exposure to 0.5 μM ouabain. The KR12 line was found to secrete human light chain constitutively and was eliminated from further consideration as a partner cell candidate. Approximately 50% of MFP-2 cells and Karpas 707H cells survived after seven days of selection. Although some literature suggested K6H6/B5 cells were resistant to ouabain, the inventors found in preliminary experiments that the line was sensitive to 0.5 μM ouabain. They did not further evaluate K6H6/B5, since ouabain resistance is required for selection of hybridomas following fusion with EBV-transformed B cells.

The inventors tested the resistance and sensitivity of myeloma partner cell lines to medium containing HAT and found that all cell lines were sensitive to the drug combination. EBV-transformed B cells were resistant to the HAT selection medium. Therefore, Sp2/0mIL-6 (hTERT), SDH-D33, and HMMA 2.5 cells were found to have preferred features for use in this work, namely they are non-secreting, ouabain-resistant HAT-sensitive lines. These three lines were used as partner cell lines in subsequent fusion studies. The selection medium was finally formulated as HAT plus 0.5 μM ouabain.

Synthetic oligodeoxynucleotides (ODNs) that contain immunostimulatory CpG motifs trigger an immunomodulatory cascade that involves B and T cells, natural killer cells and professional antigen-presenting cells. The inventors added CpG ODNs to the EBV transformation medium for human B cells. They confirmed that the addition of CpG ODNs during EBV transformation performed in tissue culture flasks did significantly enhance the efficiency of transformation, and shortened transformation times by five to ten days. In order to enrich for the percentage of antigen-specific B cell numbers in pre-fusion B cell samples, the inventors transformed smaller numbers of human B cells in multiple wells of 384-well plates using CpG and EBV. The results indicated that addition of CpG remarkably increased efficiency of EBV transformation of human B cells.

The inventors compared the relative fusion abilities of three partner cell lines, Sp2/0 mL-6 (hTERT), SHM-D33 and HMMA 2.5 to form hybridoma cells with EBV-transformed human B lymphocytes. First, the inventors compared the fusion efficiency of different myeloma partner cell lines with the same batch of EBV-transformed human B cells. The inventors then compared the fusion efficiency of a particular partner cell line with different batches of EBV-transformed human B cells. The electrofusion protocol applied used a single DC pulse of 300V. A total of $3\times10^6$ transformed B cells was used in the fusion with a cell ratio of 2:1 (partner cell: transformed B cells). Hybridoma cells were selected in medium containing HAT plus 0.5 μM ouabain for seven days in 96-well plates. The number of hybridoma colonies for each condition was counted after 15-20 days of culture after fusion. The results suggested that HMMA 2.5 was the most suitable partner cell line for generation of human hybridoma cells when electrofusion was used. The inventors therefore used this cell line for further optimization of the electrofusion protocol.

The inventors tested whether multiple direct current electrical pulses could enhance the overall fusion efficiency. HMMA 2.5 cells were fused with EBV-transformed human B cells to compare the effect of single or multiple pulses. The overall fusion efficiency decreased slightly when using multiple pulses, compared to a single pulse procedure. The addition of an alternating current wave between multiple pulses, to hold B cells and myeloma cells in contact prior to repeat pulses, did not affect this reduction in fusion efficiency. This negative effect likely was due to increased lysis of myeloma partner cells following multiple pulses. The inventors used a single pulse for subsequent experiments.

C. Engineering of Antibody Sequences

Various methods may be employed for the cloning an expression of human light and heavy chain sequences. Wardemann et al. (2003), incorporated herein by reference, describes in detail methods that may be used. Other techniques, such as those described by Takekoshi et al. (2001), are also useful. In that reference, total cellular RNA was isolated from pelleted cells using a commercial kit (RNeasy mini kit, Qiagen). Using random 9-mers, nucleotides and reverse transcriptase (Takara, RNA-PCR kit, Ohtsu), cDNAs were synthesized and were amplified by the polymerase chain reaction (PCR), with heavy and light chain primers specific for human immunoglobulins (Ig). A "touchdown" PCR protocol was employed, i.e., three cycles each of denaturation at 95° C. for 1 min, annealing for 1 min, and elongation at 72° C. for 2 min, for a total of 11 cycles. The annealing temperature was varied from 65 to 55° C. in steps of 1° C. The touchdown cycles were followed by 25 cycles using an annealing temperature of 55° C. The resultant PCR product was gel-purified in agarose and extracted using Qiaquick spin-columns (Qiagen). The light chain and heavy chain Fd genes were then cloned into the NheI/AscI and the SfiI/NotI sites of the expression vector pFabl-His2. The ligated pFab1-His2 vectors with the light chain (κ and λ) and Fd heavy chain genes (γ and μ) were introduced into competent *E. coli* JM109 cells (Toyobo, Osaka). After transformation, the *E. coli* cells were plated onto Luria-Bertani (LB)/ampicillin (50 μg/ml) plates. Isolated bacterial colonies were incubated at 30° C. in 2 ml of Super Broth (SB) with ampicillin (50 μg/ml) and $MgCl_2$ (1.5 mM). Isopropyl-β-D-thiogalactopyranoside (IPTG) was used to induce production of the Fab protein. Cells from the bacterial cultures were pelleted, resuspended in 0.3 ml of B-PER (Pierce) with a protease inhibitor cocktail (Complete, Boehringer Mannheim), and shaken for 5 min at room temperature. Cell lysates were centrifuged at 15,000 xg for 10 min, and the resultant supernatant containing the Fab antibody was collected.

The foreogoing examples are purely exemplary in nature and a variety of other methods may be employed.

IV. Passive Immunization with Anti-RSV Antibodies

While a vaccine might prevent RSV infection, no vaccine is yet licensed for this indication. A major obstacle to vaccine development is safety. A formalin-inactivated vaccine, though immunogenic, unexpectedly caused a higher and more severe incidence of lower respiratory tract disease due to RSV in immunized infants than in infants immunized with a similarly prepared trivalent parainfluenza vaccine (Kim et al., 1969; and Kapikian et al., 1969). Several candidate RSV vaccines have been abandoned and others are under development (Murphy et al., 1994), but even if safety issues are resolved, vaccine efficacy must also be improved. A number of problems remain to be solved. Immunization would be required in the immediate neonatal period since the peak incidence of lower respiratory tract disease occurs at 2-5 months of age. The immaturity of the neonatal immune response together with high titers of maternally acquired RSV antibody may be expected to reduce vaccine immunogenicity in the neonatal period (Murphy et al., 1988; and Murphy et al., 1991). Finally, primary RSV infection and disease do not protect well against subsequent RSV disease (Henderson et al., 1979).

Currently, the only approved approach to prophylaxis of RSV disease is passive immunization. Initial evidence suggesting a protective role for IgG was obtained from observations involving maternal antibody in ferrets (Suffin et al., 1979) and humans (Lambrecht et al., 1976; Glezen et al., 1981). Hemming et al. (More et al., 1986) recognized the possible utility of RSV antibody in treatment or prevention of RSV infection during studies involving the pharmacokinetics of an intravenous immune globulin (IVIG) in newborns suspected of having neonatal sepsis. They noted that 1 infant, whose respiratory secretions yielded RSV, recovered rapidly after IVIG infusion. Subsequent analysis of the IVIG lot revealed an unusually high titer of RSV neutralizing antibody. This same group of investigators then examined the ability of hyperimmune serum or immune globulin, enriched for RSV neutralizing antibody, to protect cotton rats and primates against RSV infection (Prince et al, 1985; Prince et al., 1990; Hemming et al., 1985; Prince et al., 1983; and Prince et al., 1985). Results of these studies suggested that RSV neutralizing antibody given prophylactically inhibited respiratory tract replication of RSV in cotton rats. When given therapeutically, RSV antibody reduced pulmonary viral replication both in cotton rats and in a nonhuman primate model. Furthermore, passive infusion of immune serum or immune globulin did not produce enhanced pulmonary pathology in cotton rats subsequently challenged with RSV.

Recent clinical studies have demonstrated the ability of this passively administered RSV hyperimmune globulin (RSV IVIG) to protect at-risk children from severe lower respiratory infection by RSV (Groothius et al., 1993; and The PREVENT Study Group, 1997). While this is a major advance in preventing RSV infection, this treatment poses certain limitations in its widespread use. First, RSV IVIG must be infused intravenously over several hours to achieve an effective dose. Second, the concentrations of active material in hyperimmune globulins are insufficient to treat adults at risk or most children with comprised cardiopulmonary function. Third, intravenous infusion necessitates monthly hospital visits during the RSV season. Finally, it may prove difficult to select sufficient donors to produce a hyperimmune globulin for RSV to meet the demand for this product. Currently, only approximately 8% of normal donors have RSV neutralizing antibody titers high enough to qualify for the production of hyperimmune globulin.

One way to improve the specific activity of the immunoglobulin would be to develop one or more highly potent RSV neutralizing MAbs. Such MAbs should be human or humanized in order to retain favorable pharmacokinetics and to avoid generating a human anti-mouse antibody response, as repeat dosing would be required throughout the RSV season. Two glycoproteins, F and G, on the surface of RSV have been shown to be targets of neutralizing antibodies (Murphy et al., 1994). These two proteins are also primarily responsible for viral recognition and entry into target cells; G protein binds to a specific cellular receptor and the F protein promotes fusion of the virus with the cell. The F protein is also expressed on the surface of infected cells and is responsible for subsequent fusion with other cells leading to syncytia formation. Thus, antibodies to the F protein may directly neutralize virus or block entry of the virus into the cell or prevent syncytia formation. Although antigenic and structural differences between A and B subtypes have been described for both the G and F proteins, the more significant antigenic differences reside on the G glycoprotein, where amino acid sequences are only 53% homologous and antigenic relatedness is 5% (Walsh et al., 1987; and Johnson et al., 1987). Conversely, antibodies raised to the F protein show a high degree of cross-reactivity among subtype A and B viruses. Beeler and Coelingh (1989) conducted an extensive analysis of 18 different murine MAbs directed to the RSV F protein. Comparison of the biologic and biochemical properties of these MAbs resulted in the identification of three distinct antigenic sites (designated A, B, and C). Neutralization studies were performed against a panel of RSV strains isolated from 1956 to 1985 that demonstrated that epitopes within antigenic sites A and C are highly conserved, while the epitopes of antigenic site B are variable.

A humanized antibody directed to an epitope in the A antigenic site of the F protein of RSV, SYNAGIS® (palivizumab), is approved for intramuscular administration to pediatric patients for prevention of serious lower respiratory tract disease caused by RSV at recommended monthly doses of 15 mg/kg of body weight throughout the RSV season (November through April in the northern hemisphere). SYNAGIS® is a composite of human (95%) and murine (5%) antibody sequences. See, Johnson et al., 1997 and U.S. Pat. No. 5,824,307, the entire contents of which are incorporated herein by reference. The human heavy chain sequence was derived from the constant domains of human $IgG_1$ and the variable framework regions of the VH genes or Cor (Press et al., 1970) and Cess (Takashi et al., 1984). The human light chain sequence was derived from the constant domain of Cκ and the variable framework regions of the VL gene K104 with Jκ-4 (Bentley et al., 1980). The murine sequences derived from a murine monoclonal antibody, Mab 1129 (Beeler et al., 1989), in a process which involved the grafting of the murine complementarity determining regions into the human antibody frameworks.

Although SYNAGIS® has been successfully used for the prevention of RSV infection in pediatric patients, multiple intramuscular doses of 15 mg/kg of SYNAGIS® is required to achieve a prophylactic effect. In pediatric patients less than 24 months of age, the mean half-life of SYNAGIS® has been shown to be 20 days and monthly intramuscular doses of 15 mg/kg have been shown to result in a mean+/−standard derivation 30 day serum titer of 37.+−0.21 µg/ml after the first injection, 57.+−0.41 µg/ml after the second injection, 68.+−0.51.mu.g/ml after the third injection, and 72.+−0.50 µg/ml after the fourth injection (The IMpact RSV Study Group, 1998). Serum concentrations of greater than 30 µg/ml have been shown to be necessary to reduce pulmonary RSV replication by 100 fold in the cotton rat model of RSV infection. However, the administration of multiple intramuscular doses of 15 mg/kg of antibody is inconvenient for the patient. Thus, a need exists for antibodies that immunospecifically bind to a RSV antigen, which are highly potent, have an improved pharmacokinetic profile, and thus have an overall improved therapeutic profile. Further, a need exists for antibodies that immunospecifically bind to a RSV antigen and that require less frequent administration.

U.S. Pat. Nos. 5,824,307, 5,922,344, 6,685,942, 6,818,216 and 6,855,493, all incorporated by reference, describe compositions and methods relating to the use of anti-RSV antibodies to treat or prevent RSV infections, including but not limited to, dosing regimens, routes of administration and formulations.

A. Formulation and Administration

The present invention provides pharmaceutical compositions comprising anti-RSV antibodies. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

In a particular embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. Combination Therapy

In order to increase the effectiveness of the antibody therapy of the present invention, it may be desirable to combine this treatment with other agents effective at treating or preventing RSV infections, e.g., Ribavarin®, SYNAGIS®, Numax™, oxygen, β2 agonists (such as albuterol) or corticosteroids. This process may involve administering to the patient the antibody of the present invention the other agent(s) at the same time. This may be achieved by use of a single pharmaceutical composition that includes both agents, or by administering two distinct compositions at the same time, wherein one composition includes the antibody of the present invention and the other includes the second agent(s).

The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, the antibody treatment of the present invention is "A" and the secondary treatment is "B":

```
A/B/A  B/A/B  B/B/A  A/A/B  A/B/B  B/A/A  A/B/B/B

B/A/B/B  B/B/B/A  B/B/A/B  A/A/B/B  A/B/A/B  A/B/B/A

B/B/A/A  B/A/B/A  B/A/A/B  A/A/A/B  B/A/A/A  A/B/A/A

A/A/B/A
```

Administration of the secondary agent will follow general protocols for that drug, taking into account the toxicity, if any. It is expected that the treatment cycles would be repeated as necessary.

V. Antibody Conjugates

Antibodies of the present invention may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemilluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938, 948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

VI. Immunodetection Methods

In still further embodiments, the present invention concerns immunodetection methods for binding, purifying, removing, quantifying and otherwise generally detecting RSV and its associated antigens. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of RSV antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing RSV, and contacting the sample with a first antibody in accordance with the present invention, as the case may be, under conditions effective to allow the formation of immunocomplexes.

These methods include methods for purifying RSV or related antigens from a sample. The antibody will preferably be linked to a solid support, such as in the form of a column matrix, and the sample suspected of containing the RSV or antigenic component will be applied to the immobilized antibody. The unwanted components will be washed from the column, leaving the RSV antigen immunocomplexed to the immobilized antibody, which is then collected by removing the organism or antigen from the column.

The immunobinding methods also include methods for detecting and quantifying the amount of RSV or related components in a sample and the detection and quantification of any immune complexes formed during the binding process. Here, one would obtain a sample suspected of containing RSV or its antigens, and contact the sample with an antibody that binds RSV or components thereof, followed by detecting and quantifying the amount of immune complexes formed under the specific conditions. In terms of antigen detection, the biological sample analyzed may be any sample that is suspected of containing RSV or RSV antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to RSV or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the RSV or RSV antigen is added to the wells. After binding and washing to remove non-specifically bound immune complexes, the bound antigen may be detected. Detection may be achieved by the addition of another anti-RSV antibody that is linked to a detectable label. This type of ELISA is a simple "sandwich ELISA." Detection may also be achieved by the addition of a second anti-RSV antibody, followed by the addition of a third antibody that has binding affinity for the second antibody, with the third antibody being linked to a detectable label.

In another exemplary ELISA, the samples suspected of containing the RSV or RSV antigen are immobilized onto the well surface and then contacted with the anti-RSV antibodies of the invention. After binding and washing to remove non-specifically bound immune complexes, the bound anti-RSV antibodies are detected. Where the initial anti-RSV antibodies are linked to a detectable label, the immune complexes may be detected directly. Again, the immune complexes may be detected using a second antibody that has binding affinity for the first anti-RSV antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present invention contemplates the use of competitive formats. This is particularly useful in the detection of RSV antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled RSV monoclonal antibodies to determine the amount of RSV antibodies in a sample. The basic format would include contacting a known amount of RSV monoclonal antibody (linked to a detectable label) with RSV antigen or organism. The RSV antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

2. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

3. Immunodetection Kits

In still further embodiments, the present invention concerns immunodetection kits for use with the immunodetection methods described above. As the RSV antibodies are generally used to detect RSV or RSV antigens, the antibodies will be included in the kit. The immunodetection kits will thus comprise, in suitable container means, a first antibody that binds to RSV or RSV antigen, and optionally an immunodetection reagent.

In certain embodiments, the RSV antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention.

The kits may further comprise a suitably aliquoted composition of the RSV or RSV antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present invention will also typically include a means for containing the antibody, antigen, and any other reagent containers in close confinement for commercial sale. Such containers may include injection or blow-molded plastic containers into which the desired vials are retained.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Peripheral blood mononuclear cells were isolated from eight donors by density gradient centrifugation from fresh blood, followed by distribution of cells with approximately 1000 B cells per well at the time of plating in 384-well cell culture plates containing medium with CpG ODN 10103 (Coley Pharmaceuticals) and Epstein Barr virus (supernate from ATCC cell line B95.8) to induce transformation of B cells. The inventors isolated B lymphoblastic cell lines from the transformation of blood from a healthy subject and tested supernatants by ELISA for the presence of antibodies binding to RSV F protein. The inventors collected cells from the wells corresponding to supernates exhibiting the highest level of specific binding to the RSV F protein and fused them to the HMMA2.5 nonsecreting myeloma partner (Posner) using an electrofusion technique and then distributed into 96-well culture plates in medium containing drugs to select against survival of unfused B cells or myeloma cells (HAT and ouabain). When hybridoma lines formed colonies in the presence of selecting drugs, the supernates were tested for reactivity to the RSV F protein by ELISA. Cell lines from reactive wells were cloned by limiting dilution.

Example 2

Results and Discussion

Figure 1:
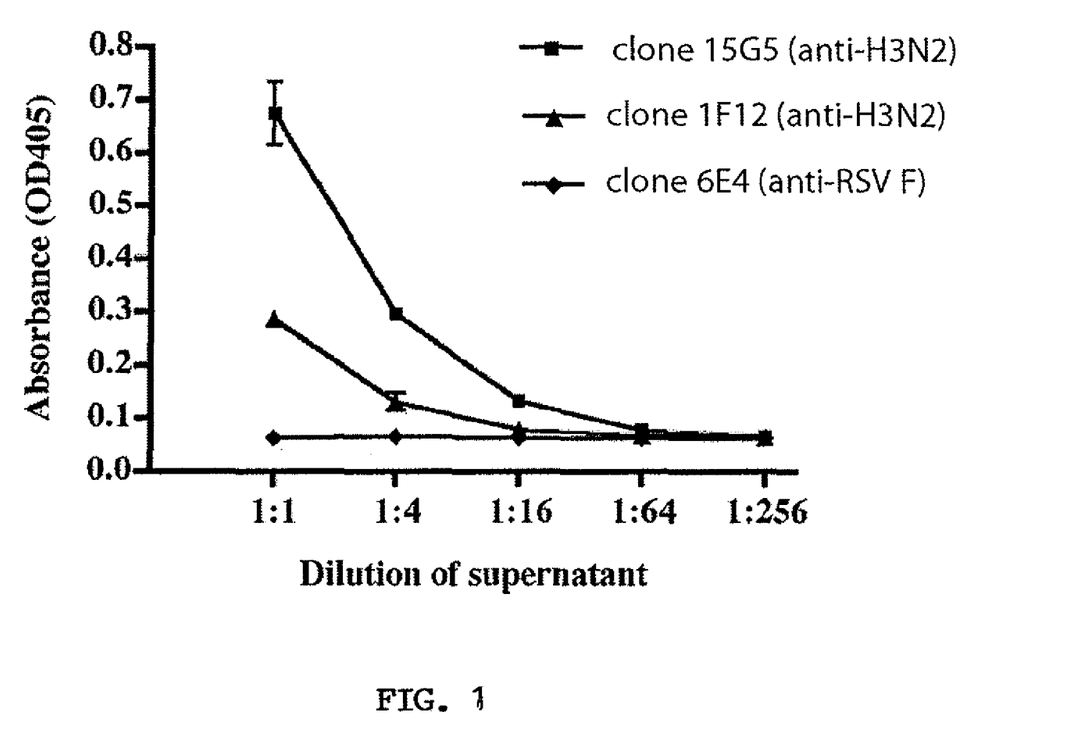
FIG. 1—Detection of antigen-specific binding for anti-H3N2 mAbs. The 15G5 and 1F12 clones were determined to be H3N2-specific during preliminary screening of cell lines. After sub-cloning, they were incubated in 24 well-plates for 1 week, then the H3N2-binding ability of the clones was tested by ELISA. The negative control antibody was an anti-RSV F human mAb.
Figure 2:
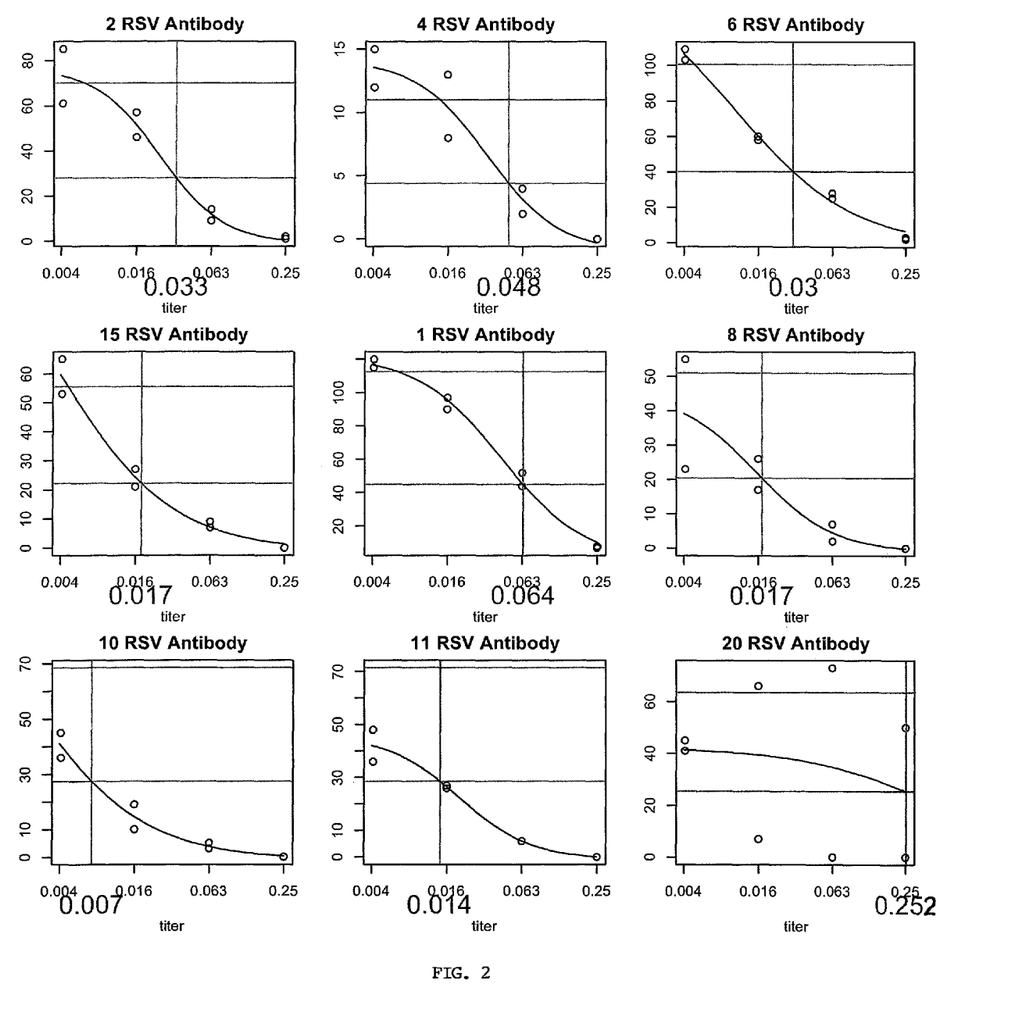
FIG. 2—RSV G8 monoclonal antibody in plaque reduction assays against a panel of antigenically diverse field strains of RSV to determine the breadth of activity. The inventor tested the following four antigenic subgroup A strains: RSV A Sw/343/'67 (designated #2), RSV Aus/A1/'61 (designated #4), RSV A SW/669/'59 (designated #6), and RSV OK/9970/'85 (designated #15). The inventor tested the following five B stains: RSV B SL863/'84 (designated #1), RSV B Wash/18537/'62 (designated #8), RSV B WV/1293'75 (designated #10), RSV B WV/5154/'80 (designated #11), and RSV B WV/401R (designated #20). The antibody exhibited a high titer of neutralizing activity against every strain tested, indicating broad activity.

The inventors isolated hybridoma cell lines from the donor that secreted antibodies reactive with the RSV F protein and then cloned the lines by limiting dilution, yielding the hybridoma designated RSV G8. Supernates from this cell line were shown to contain antibodies that bound to RSV infected cells, or to cells transfected with RSV F protein, but not to uninfected cells or cells transfected with fusion proteins from related viruses (FIG. 1). Purified human IgG from the supernate of G8 was tested in a plaque reduction assay using the RSV wild-type strain A2 and the antibody exhibited a high level of virus neutralizing activity. As shown in FIG. 2, the inventor tested four antigenic subgroup A strains —RSV A Sw/343/'67 (designated #2), RSV Aus/A1/'61 (designated #4), RSV A SW/669/'59 (designated #6), and RSV OK/9970/'85 (designated #15)—and five B stains—RSV B SL863/'84 (designated #1), RSV B Wash/18537/'62 (designated #8), RSV B WV/1293'75 (designated #10), RSV B WV/5154/'80 (designated #11), and RSV B WV/401R (designated #20).

The antibody exhibited a high titer of neutralizing activity against every strain tested, indicating broad activity.

Example 3

Antibody Sequence Information

RNA was extracted from the hybridoma and RT-PCR and cloning methods were used to determine the unique antibody genes used to encode this novel human monoclonal antibody that neutralizes RSV. The sequences identified were:

RSV F mAb G8 heavy chain
(SEQ ID NO: 1)
GAGGTGCAGCTGGTGGAGTCTGGGGGAGGCTTGGCACAGCCTGGGGGTC

CCTGACACTCGCCTGTGCAGCCTCTGGATTCACCTTCACTAGTTATAACA

TGCACTGGGTCCGCCAGGCTCCGGGGAAGGGGCTGGAGTGGGTTTCATAC

ATTACTAGTAATAGTCTTAACATATACTACGCAGACTCTGTGAAGGGCCG

ATTCACCATCTCCAGAGACAATGCCAAGAATTCACTGTATCTGCGAATGC

ACAGCCTGAGCGACGAGGACACGTCTGTGTATTACTGTGCGCGAGACTCG

TCCGGCAGTATTGGCTGGTCCGACCCCCTTGATTACTGGGGCCAGGGAAC

CCTGGTCACCGTCTCCTCAGCCGGTACCAA

RSV F mAb G8 light chain
(SEQ ID NO: 3)
GATATTGTGCTGACTCAGACTCCAGGCACCCTGTCTGTATCTCCAGGGGA

AAGAGCCACCCTCTCCTGCAGGGCCAGCCAGAGCGTTAGCAGCAATTTAG

CCTGGTACCAGCAGAAACCTGGGCAGGCTCCCAGGCTCCTCATCTCTGGT

GCATCCACCAGGGCCACTGGTATCCCAGCCAGGTTCAGTGGCAGTGGGTC

TGGGACAGAGTTCACTCTCACCATCAGCAGCCTACAGTCTGAAGATTTTG

CAGTCTATTACTGTCAGCAGTATAATTACTGGCCTCCGTGGACGTTCGGC

CAAGGGACCAAGCTGGAGATCAAACGTACTGTG

The heavy chain variable gene segments identified were VH3-48*02, D6-19*01, J4*02. It should be noted that the use of these gene segments distinguishes this antibody from all previously described human monoclonal antibodies that neutralize RSV, including Fab19 (VH3-21*01,D6-6*01,J4*02, and Fab11 (VH3-23*01,D3-3*01,J6*03), and Fab F2-5 (VH3-49*03,D2-2*01,J4*02, and Brams#19 (VH2-70*01, D3-22*01,J4*02). The light chain variable gene segments identified were VK3-15*01, JK1*01. The light chain is a kappa chain. The isotype and subclass of the RSV G8 antibody were determined experimentally and found to be IgG1.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,816,567
U.S. Pat. No. 4,867,973
U.S. Pat. No. 4,938,948
U.S. Pat. No. 5,021,236
U.S. Pat. No. 5,196,066
U.S. Pat. No. 5,565,332
U.S. Pat. No. 5,824,307
U.S. Pat. No. 5,922,344
U.S. Pat. No. 6,685,942
U.S. Pat. No. 6,818,216
U.S. Pat. No. 6,855,493

"Antibodies: A Laboratory Manual," Cold Spring Harbor Press, Cold Spring Harbor, N.Y., 1988.
Abbondanzo et al., *Am. J. Pediatr. Hematol. Oncol.*, 12(4), 480-489, 1990.
Allred et al., *Arch. Surg.*, 125(1), 107-113, 1990.
Atherton et al., *Biol. of Reproduction*, 32, 155-171, 1985.
Beeler and Coelingh, *J. Virol.*, 7:2941-2950, 1989.
Beeler et al., *J. Virology*, 63:2941-2950, 1989.
Bentley et al., *Nature*, 288:5194-5198, 1980.
Brown et al., *J. Immunol. Meth.*, 12; 130(1), :111-121, 1990.
Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
De Jager et al., *Semin. Nucl. Med.* 23(2), 165-179, 1993.
Dholakia et al., *J. Biol. Chem.*, 264, 20638-20642, 1989.
Doolittle and Ben-Zeev, *Methods Mol. Biol.*, 109, :215-237, 1999.
Fisher et al., *J. Infect. Dis.*, 180:708-713, 1999.
Gefter, Margulies, Scharff, *Somatic Cell Genet.*, 3:231-236, 1977.
Glezen et al., *J. Pediatr.*, 98:708-715, 1981.
Goding, In: *Monoclonal Antibodies: Principles and Practice*, 2d ed., Orlando, Fla., Academic Press, 60-61, 65-66, 71-74, 1986.
Graham et al., *J. Infect. Dis.*, 171:1468-1474, 1995.
Graham et al., *Pediatr. Res.*, 34:167-172, 1993.
Groothius et al., *New Engl. J. Med.*, 329:1524-1530, 1993.
Gruber et al, *Pediatr. Res.*, 21:270-274, 1987.
Gulbis and Galand, *Hum. Pathol.* 24(12), 1271-1285, 1993.
Hemming et al., *J. Infect. Dis.*, 152:1083-1087, 1985.
Henderson et al., *New Engl. J. Med.*, 300:530-534, 1979.
Hertz et al., *Medicine*, 68:269-281, 1989.
Johnson et al., *J. Infect. Diseases*, 176:1215-1224, 1997.
Johnson et al., *Proc. Natl. Acad. Sci. USA*, 84:5625-5629, 1987.
Kapikian et al, *Am. J. Epidemiol.*, 89:405-421, 1969.
Khatoon et al., *Ann. of Neurology*, 26, 210-219, 1989.
Kim et al., *Am. J. Epidemiol.*, 89:422-434, 1969.
King et al., *J. Biol. Chem.*, 269, 10210-10218, 1989.
King, Jr. et al., *Ped. Infect. Dis. J.*, 12:733-739, 1993.
Kohler and Milstein, *Eur. J. Immunol.*, 6, 511-519, 1976.

Kohler and Milstein, *Nature*, 256, 495-497, 1975.
Lambrecht et al, *J. Infect. Dis.*, 134:211-217, 1976.
More et al., In: *Clinical Use of Intravenous Immunoglobulins*, Academic Press, London, 285-294, 1986.
Murphy et al., *J. Virol.*, 62:3907-3910, 1988.
Murphy et al., *Vaccine*, 9:185-189, 1991.
Murphy et al., *Virus Res.*, 32:13-36, 1994.
Nakamura et al., In: *Enzyme Immunoassays: Heterogeneous and Homogeneous Systems*, Chapter 27, 1987.
O'Shannessy et al., *J. Immun. Meth.*, 99, 153-161, 1987.
Owens and Haley, *J. Biol. Chem.*, 259, 14843-14848, 1987.
Posner et al., *Hybridoma* 6, 611-625, 1987.
Potter and Haley, *Meth. Enzymol.*, 91, 613-633, 1983.
Press et al, *Biochem. J*, 117:641-660, 1970.
Prince et al., *Infect. Immun.*, 42:81-87, 1983.
Prince et al., *J. Virol.*, 55:517-520, 1985.
Prince et al., *J. Virol.*, 64:3091-3092, 1990.
Prince et al, *Virus Res.*, 3:193-206, 1985.
Suffin et al., *J. Immunol.* 123(1):10-4, 1979.
Takashi et al., *Proc. Natl. Acad. Sci. USA*, 81:194-198, 1984.
Takekoshi et al., *J Biochem (Tokyo)*, 130(2):299-303, 2001.
The IMpact RSV Study Group, *Pediatrics*, 102:531-537, 1998.
The Prevent Study Group, *Pediatrics*, 99:93-99, 1997.
Treanor and Falsey, *Antiviral Res.*, 44:79-102, 1999.
Walsh and Graham, In: *The Health and Disease*, Dolin and Wright (eds), Marcel Dekker, Inc., NY, N.Y., 7(7):162-203, 1999.
Walsh et al., *J. Infect. Dis.*, 155:1198-1204, 1987.
Wardemann et al., *Science*, 301(5638):1374-1377, 2003.
Wendt et al., *J Heart Lung Transplantation*, 14:479-485, 1995.
Wyde et al., *Antiviral Res.*, 1987; 7:211-220, 1987.

---

What is claimed is:

1. A purified nucleic acid molecule encoding a heavy chain variable region comprising:

```
                                                    (SEQ ID NO: 2)
EVQLVESGGGLAQPGGSLTLACAASGFTFTSYNMHWVRQAPGKGLEWVSY

ITSNSLNIYYADSVKGRFTISRDNAKNSLYLRMHSLSDEDTSVYYCARDS

SGSIGWSDPLDYWGQGTLVTVSSAGT.
```

2. A purified nucleic acid molecule encoding a light chain variable region comprising:

```
                                                    (SEQ ID NO: 4)
DIVLTQTPGTLSVSPGERATLSCRASQSVSSNLAWYQQKPGQAPRLLISG

ASTRATGIPARFSGSGSGTEFTLTISSLQSEDFAVYYCQQYNYWPPWTFG

QGTKLEIKRTV.
```

3. The nucleic acid of claim 1, wherein said nucleic acid is located in an expression cassette comprising a promoter operatively linked to said nucleic acid.

4. The nucleic acid of claim 2, wherein said nucleic acid is located in an expression cassette comprising a promoter operatively linked to said nucleic acid.

5. A purified antibody, single chain antibody, Fab' antibody fragment or F(ab')$_2$ antibody fragment comprising a heavy chain variable region comprising the sequence of SEQ ID NO: 2 and a light chain variable region comprising the sequence of SEQ ID NO: 4.

6. The antibody or antibody fragment of claim 5, dispersed in a pharmaceutically acceptable carrier.

7. A method of neutralizing respiratory syncytial virus (RSV) comprising contacting said virus with a purified antibody or antibody fragment comprising a heavy chain variable region comprising the sequence of SEQ ID NO: 2 and a light chain variable region comprising the sequence of SEQ ID NO: 4.

8. The method of claim 7, wherein said contacting occurs in vitro.

9. The method of claim 7, wherein said contacting occurs in vivo.

10. The method of claim 9, wherein said RSV is located in a human subject.

11. The method of claim 10, wherein said human subject is an infant or child.

12. The method of claim 10, further comprising administering to said subject an antiviral.

13. The method of claim 10, wherein said antibody or antibody fragment is administered to said subject more than once.

14. The method of claim 7, wherein said antibody is a single chain antibody.

15. The method of claim 7, wherein said antibody fragment is a Fab' or F(ab')$_2$.

16. The method of claim 9, wherein the antibody or antibody fragment is administered intravenously.

17. The method of claim 9, wherein the antibody or antibody fragment prevents or reduces the severity of infection in said subject by RSV.

18. A method of diagnosing a respiratory syncytial virus (RSV) infection in a subject comprising:
    (a) obtaining a sample from said subject;
    (b) contacting said sample with an antibody or antibody fragment comprising a heavy chain variable region comprising the sequence of SEQ ID NO: 2 and a light chain variable region comprising the sequence of SEQ ID NO: 4; and
    (c) determining the presence of an RSV antigen bound to said antibody.

19. The method of claim 18, wherein steps (b) and (c) comprise an ELISA, RIA or FIA.

20. The method of claim 18, wherein said subject is at risk of exposure to RSV.

21. The method of claim 18, wherein said subject had a previous RSV infection.

22. The method of claim 18, further comprising making a treatment and/or quarantine decision for said subject based on step (c).

* * * * *

SEQUENCE LISTING

```
<160> NUMBER OF SEQ ID NOS: 4

<210> SEQ ID NO 1
<211> LENGTH: 380
<212> TYPE: DNA
<213> ORGANISM: Homo sapiens

<400> SEQUENCE: 1
gaggtgcagc tggtggagtc tgggggaggc ttggcacagc ctgggggtc  cctgacactc     60 gcctgtgcag cctctggatt caccttcact agttataaca tgcactgggt ccgccaggct    120
ccggggaagg ggctggagtg ggtttcatac attactagta atagtcttaa catatactac    180
gcagactctg tgaagggccg attcaccatc tccagagaca atgccaagaa ttcactgtat    240
ctgcgaatgc acagcctgag cgacgaggac acgtctgtgt attactgtgc gcgagactcg    300
tccggcagta ttggctggtc cgaccccctt gattactggg gccagggaac cctggtcacc    360
gtctcctcag ccggtaccaa                                                 380

<210> SEQ ID NO 2
<211> LENGTH: 126
<212> TYPE: PRT
<213> ORGANISM: Homo sapiens

<400> SEQUENCE: 2

Glu Val Gln Leu Val Glu Ser Gly Gly Gly Leu Ala Gln Pro Gly Gly
1               5                   10                  15

Ser Leu Thr Leu Ala Cys Ala Ala Ser Gly Phe Thr Phe Thr Ser Tyr
            20                  25                  30

Asn Met His Trp Val Arg Gln Ala Pro Gly Lys Gly Leu Glu Trp Val
        35                  40                  45

Ser Tyr Ile Thr Ser Asn Ser Leu Asn Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Arg Met His Ser Leu Ser Asp Glu Asp Thr Ser Val Tyr Tyr Cys
                85                  90                  95

Ala Arg Asp Ser Ser Gly Ser Ile Gly Trp Ser Asp Pro Leu Asp Tyr
            100                 105                 110

Trp Gly Gln Gly Thr Leu Val Thr Val Ser Ser Ala Gly Thr
        115                 120                 125
```

```
<210> SEQ ID NO 3
<211> LENGTH: 333
<212> TYPE: DNA
<213> ORGANISM: Homo sapiens

<400> SEQUENCE: 3
gatattgtgc tgactcagac tccaggcacc ctgtctgtat ctccagggga aagagccacc      60
ctctcctgca gggccagcca gagcgttagc agcaatttag cctggtacca gcagaaacct     120
gggcaggctc ccaggctcct catctctggt gcatccacca gggccactgg tatcccagcc     180
aggttcagtg gcagtgggtc tgggacagag ttcactctca ccatcagcag cctacagtct     240
gaagattttg cagtctatta ctgtcagcag tataattact ggcctccgtg gacgttcggc     300
caagggacca agctggagat caaacgtact gtg                                  333

<210> SEQ ID NO 4
<211> LENGTH: 111
<212> TYPE: PRT
<213> ORGANISM: Homo sapiens

<400> SEQUENCE: 4

Asp Ile Val Leu Thr Gln Thr Pro Gly Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Ser Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Tyr Trp Pro Pro
                85                  90                  95

Trp Thr Phe Gly Gln Gly Thr Lys Leu Glu Ile Lys Arg Thr Val
                100                 105                 110
```